Sept. 25, 1951 L. BURBANK Plant Pat. 1,041
PLUM TREE
Filed June 6, 1950
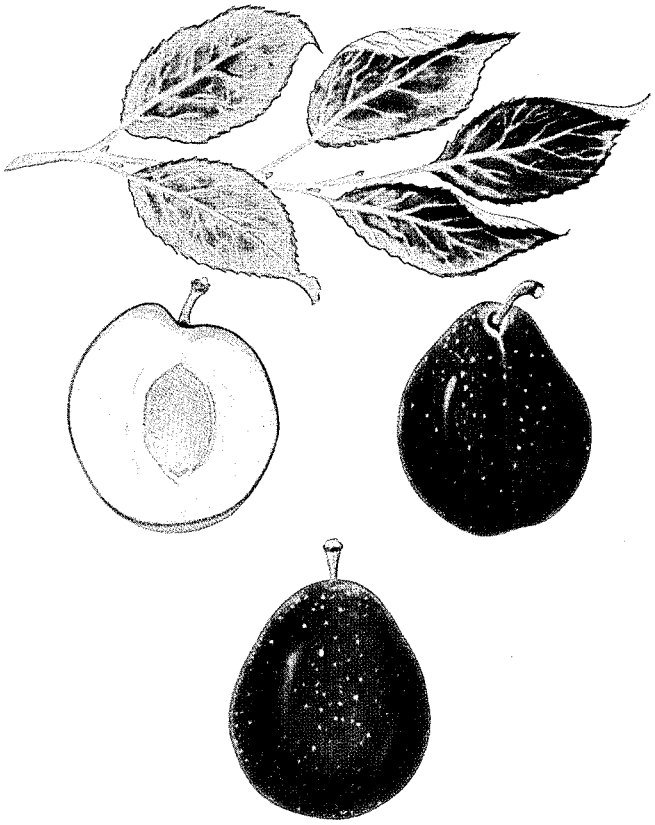
Inventor.
Luther Burbank, Deceased,
By. Elizabeth Waters Burbank,
Executrix.
By: Robert Cobb
Attorneys Patented Sept. 25, 1951

Plant Pat. 1,041

UNITED STATES PATENT OFFICE 1,041

PLUM TREE

Luther Burbank, deceased, late of Santa Rosa, Calif., by Elizabeth Waters Burbank, executrix, Santa Rosa, Calif., assignor to Stark Bro's Nurseries and Orchards Company, Louisiana, Mo., a corporation of Missouri Application June 6, 1950, Serial No. 166,464

1 Claim. (Cl. 47—62)

The present discovery relates to a new and distinct variety of plum tree, originating as a seedling resulting from deliberate cross-pollination of two varieties of unidentified parentage, as performed and propagated by the late Luther Burbank at the Burbank Experimental Gardens, at Sebastopol, California.

This new variety is distinguished from the "Italian Prune" variety (unpatented), and other prunes of Italian, German and other origin, by being a natural dwarf, with trunk and branches rougher and more stocky, and smaller leaves, and much higher productivity of fruit. The fruit ripens a week to ten days earlier than the "Italian Prune" when grown under comparable conditions, and is of superior quality, with a sweeter and more pleasing flavor, shorter stem, smaller pit cavity and smaller and smoother free stone.

These distinctive tree and fruit characteristics represent a marked improvement in plum trees, and said characteristics have been found to be established and fixed by further asexual reproduction of the variety by budding, at Louisiana, Missouri, and elsewhere.

The drawing illustrates specimens of the new plum tree foliage, branch and fruit, the latter being shown in elevation and in section with the pit in elevation.

The following is a detailed description of the new variety, giving color designations according to the conventional dictionary definition of terminology as well as corresponding color terms according to Ridgway's Color Standards and Nomenclature and Horticultural Colour Guide (observations were made near Louisiana, Missouri).

Dates first and last picking: August 30th–September 10th.

*Tree*

Small; medium vigorous; spreading; vase-formed; hardy; productive; regular bearer.

Trunk: Medium stocky; medium smooth.

Branches: Medium stocky; medium smooth; glossy to dull. Gray-Brownish Drab, Plate XLV, Colour No. 9'''', tone *m*, overlaid with Drab Gray, Plate XLVI, Colour No. 17'''', tone *d* (Ridgway).

*Lenticels.*—Few; medium large.

Leaves:

*Length.*—3 inches.

*Width.*—$1\frac{13}{16}$ inches.

Medium large; oval; abruptly pointed; thick; rugose. Dark Green-Spinach Green, Colour No. o960/1, page 187, Vol. 2 (Horticultural Color Guide).

*Margin.*—Crenate.

*Petiole.*—Medium long; medium thick.

*Glands.*—Average number, 2. Alternate; medium small; globose; free; pubescent.

Flowers: Dates first and full blossoms—April 18th–April 24th. Late compared with other varieties. Medium large; white.

*Fruit*

Maturity when described: Eating ripe August 30th.

Size: Uniform; medium large.

*Axial diameter.*—2 inches.

*Transverse in suture plane.*—$1\frac{9}{16}$ inches.

*At right angles to suture plane.*—$1\frac{3}{4}$ inches.

Form: Uniform; symmetrical; broadly ovoid; compressed transversely toward suture; sides equal.

*Suture.*—Distinct; extends from base but discontinues at apex.

*Ventral surface.*—Rounded slightly lipped toward base; lips equal.

*Cavity.*—Flaring; circular; suture showing at one side. Depth—$\frac{3}{16}$ inch. Breadth—$\frac{3}{8}$ inch. Markings—none.

*Base.*—Truncate; oblique.

*Apex.*—Rounded to truncate; depressed. Pistil point—oblique.

Stem: Length—$\frac{5}{8}$ inch. Medium stout; glabrous. Adherence to stone—strong.

Skin: Thin; tough; astringent; tenacious to flesh.

*Tendency to break.*—None in wet season or dry season.

*Color.*—Plum Purple, Colour No. 934, page 179, Vol. 2, with Spectrum Blue bloom, Colour No. 45/3, page 45, Vol. 1 (Horticultural Colour Guide).

*Down.*—Wanting.

Flesh:

*Color.*—Olive Ochre, Plate XXX, Colour No. 21'' (Ridgway).

*Amygadalin.*—Wanting. Juice—scant; rich.

*Texture.*—Meaty.

*Fibres.*—Few; fine; tender.

*Ripens.*—Fairly even.

*Flavor.*—Mild; sweet.

*Aroma.*—Wanting.

*Eating quality.*—Good.

Stone: Free.

*Fibres.*—Retains short fibrelike threads along ridges.

*Size.*—Medium small. Length, $\frac{7}{8}$ inch. Thickness, $\frac{5}{16}$ inch.

*Form.*—Oval; full toward base and apex.

*Base.*—Oblique. Hilum—oval.

*Apex.*—Rounded.

*Sides.*—Equal; curved on right and left sides; irregularly furrowed throughout.

*Ridges.*—Rounded toward base and apex.

*Pits.*—Ventral edge—thick, without wing.

*Dorsal edge.*—Narrow with deep narrow groove throughout. Ridges—on either side continuous.

Use: Market; dessert; culinary; canning.

Keeping quality: Good.

Resistance to:

*Insects.*—Medium.

*Diseases.*—Good.

Shipping quality: Good.

I claim:

A new and distinct variety of plum tree, characterized as to novelty by the natural dwarf habit of growth, rough and stocky trunk and branches, and small foliage of the tree, high productivity, early ripening and superior quality and sweet flavor of the fruit, the latter having a short stem, small pit cavity and small, smooth free stone, substantially as shown and described.

ELIZABETH WATERS BURBANK,

*Executrix of the Estate of Luther Burbank, Deceased.*

No references cited.